(12) United States Patent
Bjorksten et al.

(10) Patent No.: US 8,114,397 B2
(45) Date of Patent: *Feb. 14, 2012

(54) STABILIZED BACTERIAL FORMULATION

(75) Inventors: Bengt Bjorksten, Stockholm (SE); Bo Mollstam, Lerum (SE)

(73) Assignee: Biogaia AB, Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 12/590,313

(22) Filed: Nov. 5, 2009

(65) Prior Publication Data

US 2010/0129336 A1    May 27, 2010

Related U.S. Application Data

(62) Division of application No. 10/860,201, filed on Jun. 3, 2004, now Pat. No. 7,955,834.

(51) Int. Cl.
*A01N 63/00*    (2006.01)

(52) U.S. Cl. .................................. 424/93.45; 435/252.9

(58) Field of Classification Search .................. None
See application file for complete search history.

(56) References Cited

U.S. PATENT DOCUMENTS

| | | | | |
|---|---|---|---|---|
| 4,518,696 | A | * | 5/1985 | Gehrman et al. .......... 435/252.9 |
| 6,479,051 | B1 | * | 11/2002 | Bruce et al. ................ 424/93.45 |

OTHER PUBLICATIONS

Casas et al., Microbial Ecology in Health and Disease 200, vol. 12, 247-285.*
Shorinkova et al., JPGN, 1997, vol. 24, No. 4.*
World Conference Proceedings, 1990, Edible Fats and Oils Processing, Edited by Erickson, D.R., p. 95.*
Maliakkal et al., Current Opinion in Gastroenterology, 1992, vol. 8, Issue 2. Abstract.*
Rautava et al., J Allergy Clin Immunol 2002, 109, p. 119-121.*
Flilteau et al., Immunology, 1999, vol. 97, p. 595-600.*
McCarthy et al. , Gut, 2003, vol. 52, p. 975-980.*
Miettinen et al., Infection and Immunity, 1996, vol. 64, No. 12, p. 5403-5405.*

* cited by examiner

*Primary Examiner* — Kade Ariani
(74) *Attorney, Agent, or Firm* — Lynn E. Barber

(57) ABSTRACT

Selected strains of *Lactobacillus* and products containing cells of the selected strains to improve breast milk for feeding to babies, more precisely to increase the levels of the anti-inflammatory cytokine IL10 in the milk and reduce the risk that the feeding baby will develop allergies and simultaneously reduce the cause and thereby the amount of TGF-beta-2 in the milk, thus resulting in reduced risk for the lactating mother to develop mastitis.

8 Claims, 1 Drawing Sheet

STABILIZED BACTERIAL FORMULATION

CROSS-REFERENCE TO RELATED APPLICATIONS

This application is a divisional application of U.S. Ser. No. 10/860,201 filed Jun. 3, 2004 now U.S. Pat. No. 7,955,834.

BACKGROUND OF THE INVENTION

1. Field of the Invention

This invention relates to selection and use of lactic acid bacteria for improved breast milk for feeding to babies.

2. Description of the Related Art

The hygiene hypothesis of allergic disease suggests that environmental changes in the industrialized world have led to reduced microbial contact at an early age and thus resulted in the growing epidemic of allergic disease such as atopic eczema, allergic rhinoconjunctivitis, and asthma. One such environmental change that has been discussed is our changed ingestion of natural microbes of various kinds due to improved hygiene, standard of living, eating habits etc. This has led to shifts in the composition of our natural gut flora (Journal of Allergy and Clinical Immunology, 2001; 108: 516-520) and also changes in the composition of the breast milk of a lactating mother. Such changes have been connected to the prevalence of allergies of various kinds. It has also been reported that infants that are the later additions to larger families have a reduced risk of allergy than their siblings that were born early (the first of the brood). This can imply that the breast milk of a mother "improves" with increasing number of pregnancies.

Human milk contains a variety of components important in the immune system, such as macrophages, immunoglobulins, or antimicrobial proteins, which are thought to protect against infection and inflammation in the gastrointestinal and respiratory tract of the milk-fed offspring. In addition, the presence of other potentially immunomodulating factors (e.g., complex oligosaccharides, growth factors, enzymes, hormones, or cytokines) has been discussed. These beneficial properties together with the high availability of nutrients and the low antigen content of human milk are the physiologic basis of the current recommendation by pediatric experts that breast milk is the best food for infants, especially those with a family history of allergies.

Thus, it is known that breast milk contains a series of cytokines and chemokines that potentially could affect the development of allergy in the infant. It has previously been reported that components that modulate allergic reactions, such as cytokines, chemokines, and adhesion molecules, are secreted in milk at various stages of lactation (S Rudloff et al, Allergy 1999, 54, 206-211). Cytokines or chemokines could be either beneficial or disadvantageous to the breast-fed infant.

It is also known that cytokines delivered by the breast milk of animals have the ability to survive passage through the GI tract of the offspring. For example, homozygous TGF-beta-1-knock out mice die of widespread inflammatory disease after weaning, presumably being saved until weaning by the transfer of maternal milk delivered TGF-beta (Kulkarni A B et al., Am J Pathology 1993; 143, 3-9). The TGF-beta survives passage all the way to the colon. IL-10 probably also survives in this way and thus delivery from the breast milk allows the IL-10 to reach the GI tract and potentially induce beneficial anti-inflammatory effects.

Further, Hawkes J S et. al. (Lipids 2001 October 36:1179-81) reported that long-chain polyunsaturated fatty acids have been associated with aspects of immune regulation including cytokine production. The purpose of this study was to investigate the effect of maternal dietary supplementation with tuna oil, rich in docosahexaenoic acid (DHA), on the concentration of transforming growth factor beta 1 (TGF-beta-1) and TGF-beta-2 in breast milk. In this randomized, dietary intervention trial, mothers of term infants consumed a daily supplement of 2000 mg oil containing either placebo (n=40), 300 mg DHA (n=40), or 600 mg DHA (n=40). The DHA increase in milk and plasma was proportional to dietary DHA. There was no relationship between milk DHA status and TGF-beta-1 and TGF-beta-2 levels.

IL-10 is a well-documented and accepted anti-inflammatory cytokine. The implication is that it will have anti-inflammatory effects in the GI tract of the infant. This is good for the infant—breast milk is generally considered to be anti-inflammatory for the infant in the sense that the infant should not overreact to pathogens/infections that appear in the gut early in life. Further, animal data points to the possible benefits for the offspring of IL-10 in the milk. An Australian group looked at an animal model where the allergy to ticks was investigated. Animals which were negative to a skin prick test (SPT) for ticks had IL-10 and IL-4 production, with the IL-10 dampening the IgE (allergic response) and the animals showing no allergy. In the allergic SPT+ve (histamine) animals, only IL-4 was produced and there was no IL-10 production. Thus IgE was not lowered and the allergy prevailed. Thus IL-10 dampens the allergy-inducing effects of IgE and may prevent allergy development.

TGF-beta-2 (Transforming Growth Factor) is also a well documented growth factor/cytokine. Its sources include for example platelets that yield milligram amounts of TGF-beta/kilogram. The factor and its isoforms (see below) can also be isolated from other tissues (microgram TGF/kg) and is found predominantly in spleen and bone tissues. Human milk also contains this factor and it is synthesized also for example by macrophages (TGF-beta-1), lymphocytes (TGF-beta-1), endothelial cells (TGF-beta-1), keratinocytes (TGF-beta-2), granulosa cells (TGF-beta-2), chondrocytes (TGF-beta-1), glioblastoma cells (TGF-beta-2), leukemia cells (TGF-beta-1).

Depending upon the cell type and conditions, the secretion of TGF-beta can be induced by a number of different stimuli including steroids, retinoids, EGF (Epidermal Growth Factor), NGF, activators of lymphocytes, vitamin D3, and IL1. The synthesis of TGF-beta can be inhibited by EGF, FGF (Fibroblast Growth Factor), dexamethasone, calcium, retinoids and follicle stimulating hormone. TGF-beta also influences the expression of its own gene and this may be important in wound healing. TGF-beta exists in at least five isoforms, known as TGF-beta-1, TGF-beta-2, TGF-beta-3, TGF-beta-4, TGF-beta-5, that are not related to TGF-alpha. The amino acid sequences of these isoforms display homologies on the order of 70-80 percent. TGF-beta-1 is the prevalent form and is found almost ubiquitously while the other isoforms are expressed in a more limited spectrum of cells and tissues. Isoforms isolated from different species are evolutionarily closely conserved and have sequence identities on the order of 98 percent. Mature human, porcine, simian and bovine TGF-beta-1 are identical and differ from murine TGF-beta-1 in a single amino acid position. Human and chicken TGF-beta-1 are also identical.

It has further been reported that members of the transforming growth factor beta (TGF-beta) family are pleiotropic cytokines with key roles in tissue morphogenesis and growth (Ingman W V, Bioessays 2002 October 24:904-14). TGF-beta-1, TGF-beta-2 and TGF-beta-3 are abundant in mammalian reproductive tissues, where development and cyclic remodeling continue in post-natal and adult life. Potential roles for TGF-beta have been identified in gonad and secondary sex organ development, spermatogenesis and ovarian function, immunoregulation of pregnancy, embryo implantation and placental development.

Rautava et. al. in Journal of Pediatric Gastroenterology and Nutrition 38:378-388, April 2004, states that TGF-beta-2 and IL-10 appear to function in a synergistic fashion with TGF-beta-2 favoring the production of IL10.

Mastitis is an inflammation of the breast that is often characterized by tenderness and erythema and sometimes fever, and is related to TGF-beta-2. During mastitis, the tight junctions of mammary alveolar cells open up, and this process is accompanied by an increase in sodium, inflammatory cells, and inflammatory and immunological mediators in breast milk. Mastitis is usually unilateral, and the highest incidence is in the first several weeks of breastfeeding. In industrialized countries, mastitis has generally been considered a problem of low morbidity, as affected women are often treated by midwives and nurse practitioners. Mastitis appears to be more common than previously believed, as large, longitudinal studies that have followed lactating women in the USA, Finland, and Australia (Semba R., Annals of the New York Academy of Sciences. November 2000; 918:156-62) suggest that 20-33% of women may develop clinically apparent mastitis. The number of lactating women with sub-clinical mastitis is logically therefore even greater.

Also mastitis has recently been linked with higher human immunodeficiency virus (HIV) load in breast milk and higher risk of mother-to-child transmission of HIV. (Semba, R. D., N. Kumwenda, T. E. Taha, et al. 1999. Mastitis and immunological factors in breast milk of human immunodeficiency virus-infected women. J. Hum. Lact. 15 (4): 301-306).

TGF-beta-2 in breast milk is mostly from epithelial origin even if it is synthesized by many other cells, including B- and T-cells. Therefore increased level of TGF-beta-2 could be a mediator of or an effect of a sub-clinical breast inflammation. The ratio of sodium and potassium in breast milk (Na/K ratio) is said to be a well known predictor of infection and sub-clinical breast inflammation.

Also, Kalliomaki et. al. in J Allergy Clin Immunol. 1999 December; 104 (6):1251-7, has suggested that TGF-beta in colostrum may prevent the development of allergic disease during exclusive breast-feeding and promote specific IgA production in human subjects.

Further, various locations of the body of humans and other mammals are inhabited by many different species of bacteria, including a number of different species of *Lactobacillus*. Such bacteria many times coexist with their host giving synergistic beneficial effects of various kinds, nowadays also known to be diverse and dependent upon the actual strain of bacteria. Different lactic acid bacteria strains, for example, *L. reuteri* SD2112, have specific antigens either on their surface or released by the bacterium in the gastro-intestinal tract of the mother. The data in Valeur et al, AEM, 70, 1176-1181 (2004) shows that ingested *L. reuteri* SD2112 can affect the levels of CD4+ T-helper cells in the ileum of a healthy human as one example. Such observations have also been made in other mammalian species and avians indicating this may be a fundamental signaling system between gut flora and host. Via the so-called entero-mammary link, antigens from the active strains are actively transported to the lymph regions, i.e. the Peyer's patches, beneath the epithelium of the GI tract. Antigen-specific B-cells are then activated after which they migrate from the GI tract epithelium via the circulation to other mucosal membranes in the body including the salivary and mammary glands. The expression of specific molecules on these cells is thought to direct their adhesion to these tissues. Once in the mammary gland, these immune cells then direct other processes to determine the levels of cytokines produced locally. This type of signaling via the entero-mammary link has been demonstrated in the generation of secretory IgA in breast milk and is highly likely to apply to cytokine production also.

It has earlier been suggested (Laiho et al, Pediatric Research 53:642-647, 2003) that the observed associations between nutritional and inflammatory factors in breast milk shows that it may be possible to influence the immunologic properties of breast milk by dietary intervention of the mother. The same group noted that mothers with allergic disease had a lower concentration of TGF-beta-2 in breast milk compared with those without. In their hands IL-10 was detected, only at low levels and frequency naturally in breast milk, with no difference between mothers with allergic disease or not. It was suggested that protection from allergic disease was, mainly via induction of oral tolerance for TGF-beta-2 and IL-10, and that particularly breast milk TGF-beta-2 may play a key role with respect to the prevention of allergic disease. However, Weiner H. reported in Microbes and Infection, Volume 3, Issue 11, September 2001, pages 947-954 that because regulatory T cells generated by oral antigen are triggered in an antigen-specific fashion but suppress in an antigen-nonspecific fashion, they mediate bystander suppression when they encounter the fed autoantigen at the target organ. Thus, mucosal tolerance can be used to treat inflammatory processes that are not autoimmune in nature.

Different *Lactobacillus* species, including *Lactobacillus reuteri*, have been used in so called probiotic formulations, meaning supplying an animal, including humans, with live and beneficial microorganisms. *Lactobacillus reuteri* is one of the naturally occurring inhabitants of the gastrointestinal tract of animals, and is routinely found in the intestines, and occasionally in the birth channel, breast milk and mouth of healthy animals, including humans. It is known to have antibacterial activity. See, for example, U.S. Pat. Nos. 5,439,678, 5,458,875, 5,534,253, 5,837,238, and 5,849,289. When *L. reuteri* cells are grown under anaerobic conditions in the presence of glycerol, they produce the antimicrobial substance known as reuterin (β-hydroxy-propionaldehyde).

Lactic acid bacteria have earlier also been reported to be used to prevent and treat allergies of various sort for example can the following patent/patent applications be mentioned EP 1239032 by Stadler et al regarding new recombinant strains, WO 01/37865 by Clancy et at regarding lowering the amount of IgE by lactobacilli.

It is therefore an object of the invention to provide selected lactic acid bacteria and components thereof for improved breast milk for feeding to babies, and a method of such selection. More precisely, it is an object of the invention to increase the levels of the anti-inflammatory cytokine IL-10 in the milk for reducing the risk that the feeding baby develops allergy at the same time as reducing the cause and thereby the amount of TGF-beta-2 in the milk and the risk for the lactating mother to develop mastitis.

It is therefore one object of the invention to compensate for negative changes in microbial flora by giving specifically selected strains of lactic acid bacteria to mothers before and during breast-feeding.

It is another object of the invention to select, using the herein described method or similar distinguishing specific cytokine influence of the test strains on relevant cell types, and use such certain strains of lactic acid bacteria as dietary components for mothers that stimulates increased production of IL10 in the breast milk at the same time as reducing the TGF-beta-2 level, indicating lower level of sub-clinical inflammation in the breast milk glands and other tissue and therefore reduced risk of mastitis. Mastitis and sub-clinical mastitis can be considered to interfere with breast feeding and thus preventing benefit to the infant that breast milk provides—the selected lactobacilli by the method of the present invention then may improve mothers health and allow them to give milk for a longer time.

It is a further object of the invention to provide products containing said strains, mutants, metabolites or components thereof, including agents for administration to animals, including humans.

Other objects and advantages will be more fully apparent from the following disclosure and appended claims.

SUMMARY OF THE INVENTION

The invention herein comprises strains of *Lactobacillus*, and components thereof, that have been selected for their capability to improve breast milk for feeding to babies, more precisely to increase the levels of the anti-inflammatory cytokine IL10 in the milk for reduced risk that the feeding baby develops allergy at the same time as reducing the cause and thereby the amount of TGF-beta-2 in the milk, meaning reduced risk for the lactating mother to develop mastitis and thereby increasing the ability to give breast milk and the global protection and optimal growth it confers on the child. The invention herein also includes the method of selection of such *Lactobacillus* strains. The invention also includes a novel method to protect viable *Lactobacillus* in a formulated oil product, as a mean of delivery of the active component.

Other objects and features of the inventions will be more fully apparent from the following disclosure and appended claims.

DETAILED DESCRIPTION OF THE INVENTION AND PREFERRED EMBODIMENTS THEREOF

Figure 1:
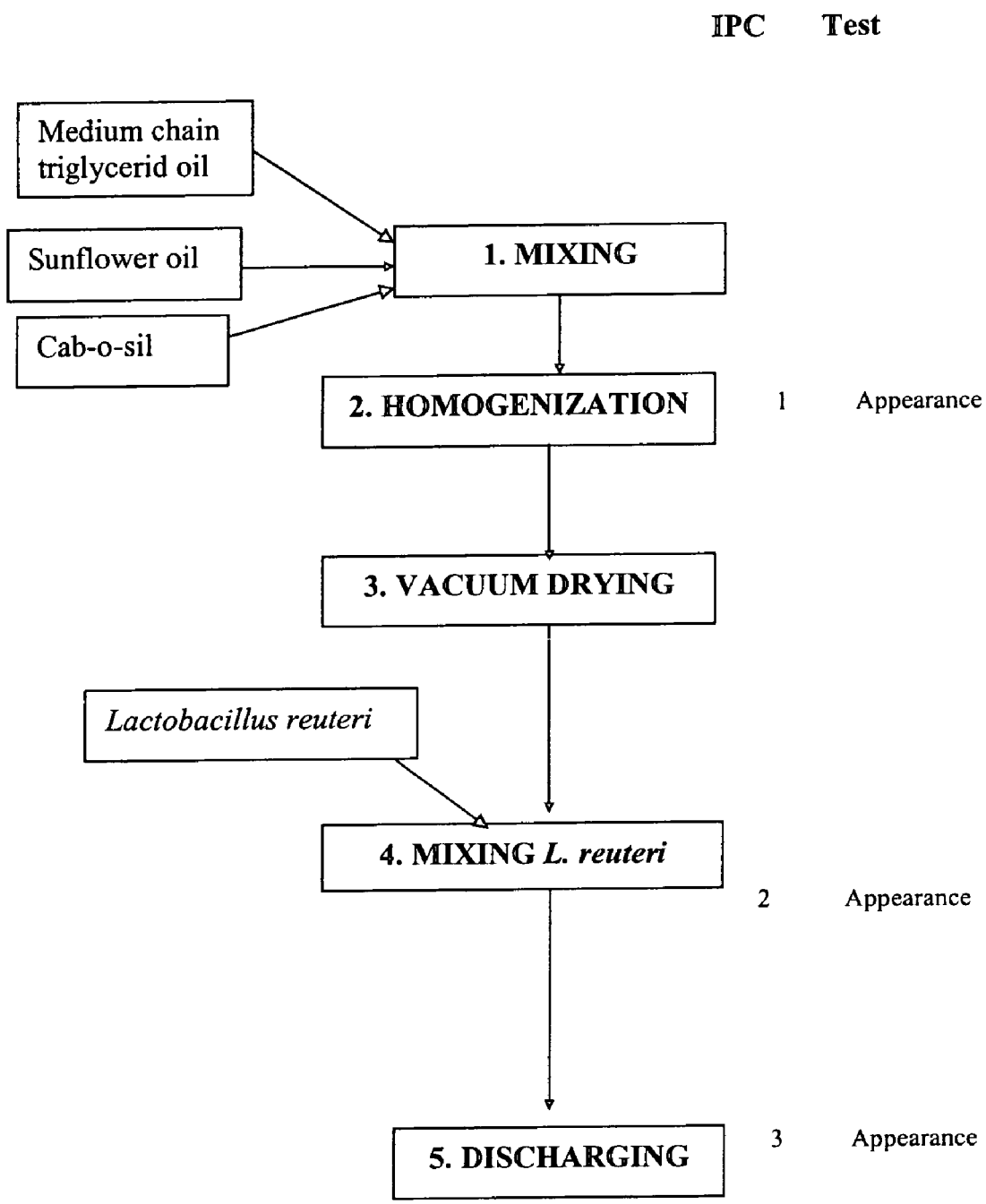
FIG. 1 is a flow chart of a manufacturing process that may be used to make the product of the invention.

The present invention provides a product to improve breast milk for feeding to babies, more precisely to increase the levels of the anti-inflammatory cytokine IL10 in the milk and reduce the risk that the feeding baby will develop allergies and simultaneously reduce the causative factors that trigger the production of the cell signaling substance (TGF) and thereby the amount of TGF-beta-2 in the milk, thus resulting in reduced risk for the lactating mother to develop mastitis. The decrease of TGF-beta-2 associated with the invention is considered to be an anti-inflammatory effect of consuming selected lactic acid bacteria meaning that the incidence of sub-clinical mastitis is lowered in the lactating group who recently had daily intake of the bacteria. An example of a strain selected by the invention herein is *L. reuteri* SD2112 (deposited on Dec. 7, 1995 in the American Type Culture Collection, now having its address at P.O. Box 1549, Manassas, Va. 20108; this strain of *Lactobacillus reuteri* has been assigned deposit/accession number ATCC 55730).

In a clinical trial in the investigation leading to this invention, there were only three factors in the analysis that were related to the level of IL-10 in the colostrum of the mothers: a) treatment or not with selected lactic acid bacteria b) the number of previous children born to the mother and c) the number of previous pregnancies. Thus, the higher the number of infants or pregnancies a mother has had, the more IL-10 is present in her colostrum. Giving specifically selected lactic acid bacteria to the expectant mother four weeks before delivery also has the ability to increase the level of IL-10 in the colostrum without the earlier pregnancies being required.

Increased systemic expression of IL-10 is in some situations also known to prevent type 1 diabetes, therefore the strains selected according to this invention could also be useful for this purpose.

In the selection method used herein, the best strains for inducing IL10 in the breast milk, and showing reduced level of TGF-beta-2, are selected by using an established mouse model and traditional analytical methods. Other similar methods of detecting cytokine production in milk can also be used. The details of this will be more clearly understood from the Examples. The product of the invention preferably contains living cells of the selected strain(s); however, if isolated metabolites or parts of such cells are responsible for the activity of the living cells of the strain(s), the products of the invention may include such metabolites or parts in addition to or instead of the living cells. The product of the invention can be any product for consumption by the woman, such as an oil drop product, food products, tablet, capsule, powder-sachet, and the like. Products lending themselves particularly to use in the invention include an oil drop (as in Example 3) that will help keeping the active ingredient stable for an extended time. *Lactobacillus* cells have been used in oil-formulations for improved stability of the bacteria, see for example U.S. Pat. No. 4,518,696 by Gehrman et al. But none of the existing formulations of lactic acid bacteria in oils and fats that we have found contains the important step of the drying the oil by the means of vacuum before formulation for increased stability of the bacteria cultures, as set forth in the examples herein.

The concentration of selected *Lactobacillus* cells needed for effectiveness of a product of the invention depends on the type of food and the amount of food to be ingested (or the time of use in the mouth of a non-food dental treatment product), but it is usually preferable to have equivalent of about $10^5$-$10^8$ CFU (colony-forming units) or more per daily intake of a product. Amounts up to about $10^{10}$-$10^{11}$ CFU are possible and can be used to increase efficacy without adversely affecting the product's organoleptic characteristics (its flavor or smell). When the product is a yogurt or other lactic acid fermentation product, the lactic acid fermentation strain(s) used to produce the product would preferably be standard cultures (e.g., in yogurt, *S. thermophilus* and *L. bulgaricus*). It is important that the selected active strain having the desired cytokine effects according to the invention herein be compatible with any standard cultures used in the product, so that the important properties of each strain used are not negated by the use of the other strain(s). This can of course be easily determined by screening tests known in the art. The strains used for the invention herein may be added either before or after the fermentation of the product at a level equivalent of about $10^6$-$10^8$ CFU per daily serving of yogurt or more as discussed above.

Preferably the product of the invention does not contain other antibacterial components, at least none that inhibit or kill selected the *Lactobacillus* strain(s), or metabolites or components thereof, or interfere with the activity.

The strain(s) of *Lactobacillus*, or metabolites or components thereof, can be an additive mixed into the ingredients by means known in the art for formulation of products of that type. When using cells and if preparation of the selected food or other product of the invention requires a heating step, the

*Lactobacillus* strain(s) should be added after the heating. Once the selected *Lactobacillus* cells are in the product, it is preferred not to heat the product to 60-70 degrees C. or above for an extended period of time.

The features of the present invention will be more clearly understood by reference to the following examples, which are not to be construed as limiting the invention.

EXAMPLE 1

Method of Selection of Strains

The selection of the *Lactobacillus* strains to be used according to this invention can be done in the following step manner:
Evaluation of Stimulation of IL10 Production and TGF-Beta-2 Reduction in Human Breast Milk by Cells of *Lactobacillus* Strains for Selection of Strains This is an example of the selection method; certain variations and alteration of this method can be made by someone skilled in the art without departing from the invention herein.
Materials and methods Animals: Fifty-one germ free BALB/c mice (males and females) are purchased from Wisconsin University, USA. Mice are shipped in sterile plastic film shippers. Fifteen mice are transferred to each of 3 isolators (isolators #2, 3, and 4). Two cages containing each one 2 males and 4 females are placed in isolator #1 (breeder).
Animal Handling Mice are maintained in sterile flexible film isolators (Class Biologically Clean, Ltd, Madison, Wis., USA). Isolators are sterilized with 2% peracetic acid (FMC Corporation, Philadelphia, Pa., USA) solution containing 0.1% Naconal (Stepan Co., Rocksport, Ill. USA). Five to 6 mice are housed in peracetic acid sterilized polystyrene cages with stainless steel wire lids. Mice of the same gender are placed in each cage. Mice are fed autoclavable Agway rodent chow 3500 (Agway, Granville, Creedmoore, N.C., USA). Food, water and bedding are autoclaved. Food and bedding are autoclaved inside stainless steel cylinders and then transferred aseptically into isolators. Bottles with tap water are autoclaved and then sterilized with peracetic acid when placed into isolators. All mice received food and water ad libitum. Food and water levels are checked daily. Bedding is changed once a week. Animals are maintained under a 12 hour light/darkness cycle. Room temperature and relative humidity are checked daily.
Bacteria Lactic acid bacteria to be tested are identified and characterized by biochemical and molecular biology techniques. The lactobacilli are first grown in 10 ml of Man-Rogosa-Sharp (MRS) medium (BBL, Cockeysville, Md.), incubated for 18 h at 37° C. and then transferred to 90 ml of MRS, incubated at 37° C. for 18 h and transferred to 1000 ml of MRS. After 18 h incubation at 37° C. the cultures are spun at 3000 rpm for 10 minutes in a refrigerated centrifuge (SORVALL RC2-B, SORVALL, Norwalk, Conn., USA), the supernatant is discarded and the pellet washed twice with sterile phosphate buffered saline (PBS) at 3000 rpm for 10 min. The pellet of each strain is re-suspended in 30 ml of PBS. The cultures are placed in 1.2-ml cryovials and stored at −70° C. until used. Before offering the bacteria to the mice, the pureness and concentration of the cultures are checked. Serial 1/10 dilutions of the lactobacilli suspensions were cultured on plates of MRS medium with 1.5% agar and incubated in anaerobe jars (GasPaK: BBL, Cockeysville, Md., USA) containing anaerobic generators (Anaero Gen: Oxoid Ltd., Wake Road, Basingstoke, Hampshire, England, GB) for 48 h at 37° C. Cultures are checked for colony morphology and reuterin production.
Tests Treatments (in this Example)
Control.
Strain: *Lactobacillus reuteri* SD2112, ATCC 55730.
Strain: *Lactobacillus* 4000
Strain: *Lactobacillus* 4020
Determination of *Lactobacillus* Colonization One day after mice are placed into the isolators, fecal samples are taken from mice in each cage to test for absence of microorganisms. Mice are deprived of water from 11:00 am to 7:00 pm. After this period of time, 1.2 ml of a lactic acid bacteria suspension is added to each bottle containing 200 ml of water and offered to mice.

Mice in isolator #2 receive *L. reuteri* SD2112. The suspension added to water contains $2.0 \times 10^{10}$ cfu/ml of *L. reuteri* SD2112. Mice in isolator #4 receive *Lactobacillus* 4000 strain and the mice in isolator #5 receive *Lactobacillus* 4020 strain. The lactic acid bacteria suspension added to each water bottle contains $3.0 \times 10^{10}$ cfu/ml. Mice in isolator #3 receive only water (control). Fecal samples (10 pellets) from mice (cage group) in each isolator are taken weekly to test for lactic acid bacteria colonization and possible contamination with other microorganisms.
"Conventionalization" with Altered Schaedler Flora Sixty days after colonization with test strains started mice are "conventionalized" with altered Schaedler flora. C3H mice bearing altered Schaedler's flora were purchased from Taconic Farms, Inc. (Germantown, N.Y., USA). Two mice are placed in each isolator and feces samples taken immediately to test for the presence of the test strain. Control mice and mice colonized with test strains are deprived of water overnight. The next day 10 feces pellets from C3H mice are placed in each bottle of drinking water, suspended in water, and offered to mice. This procedure is followed for 3 consecutive days. Feces from BALB/c and C3H mice are obtained once a week during 1 month to check for altered Schaedler flora colonization and presence of test strains
Evaluations Forty-five days after monocolonization with test strains, and 30 days after "conventionalization" five mice from each treatment group are euthanized and the animals sampled for spleens for T-lymphocytes isolation and cytokine determination.

Preparation of spleen cells: Spleens are removed aseptically and placed in cold PBS +0.5% bovine serum albumin (BSA)(Sigma Chemical Co., St Louis, Mo., USA) +0.1% sodium azide (NaN3) (Sigma). A single cell suspension from each spleen is prepared by perfusing it with 5 ml of RPMI-1640 medium (Sigma) +0.1 mg/ml of gentamicin (Sigma). The cell suspension is transferred into 15 ml sterile conical tubes and centrifuged at 2000 rpm for 10 min. in a refrigerated centrifuge. The supernatant is decanted and red blood cells from each tube lysed by resuspending the cells in 0.5 ml PBS 1×, then adding 9 ml of distilled water, mixing well, and finally adding quickly 1 ml of PBS 10× and mixing well. The suspension is centrifuged as above then the supernatant is discarded and the cells resuspended in 5 ml of RPMI-1640 complete medium. A sample of the suspension is checked under the microscope and if particles other than cells are present, the suspension is filtered through a sterile nylon cloth and centrifuged again. The pellet is resuspended in 5 ml of complete RPMI-1640 medium, washed twice, and finally resuspended in 5 ml of complete medium. The cell viability is determined by trypan blue (Sigma) exclusion. Twenty µl of cells suspension are diluted in 380 µl of 0.1% trypan blue solution (1:20 dilution) and counted in a hematocytometer. The concentration of the cell suspension is adjusted to $1.0 \times 10^6$ cells/ml in complete RPMI-1640.

Cell culture: Cells are cultured in sterile 96 well flat-bottom tissue culture plates (Fisherbrand, Fisher Scientific, Pittsburgh, Pa., USA) with RPMI-1640 complete medium in the absence (unstimulated) and in presence of inducing agents such as Concavalin A (5 µg/ml), LPS (1 µg/ml) from *Salmonella typhimurium*, phorbol 12-myristate-13-acetate (PMA; 10 ng/ml), ionomycin (I; 0.5 µg/ml), and heat inactivated *L. reuteri* (4.5 mg protein/ml). One hundred µl of cell suspension containing $1.0 \times 10^5$ cells and fifty µl of heat inactivated *L. reuteri* (4.5 mg protein/ml) are added to each well. Each set is run with 5 repetitions. The cell cultures were incubated in 5% $CO_2$ atmosphere for 48 h at 37° C. with the mitogen and for 96 h with *L. reuteri*. The supernatants from the 5 wells are collected, pooled and stored at −70° C. until used for cytokines assays.

Cytokine quantification: Cytokines (IL-10, TGF-beta-2) are measured in supernatants by ELISA using the murine Quantikine™ kit (R&D Systems, Minneapolis, Minn., USA) following the procedure recommended by the manufacturer.

Results

Cytokines are immune system proteins that are biological response modifiers. They coordinate antibody and T cell immune system interactions, and amplify immune reactivity. Cytokines include monokines synthesized by macrophages and lymphokines produced by activated T lymphocytes and natural killer (NK) cells.

*L. reuteri* SD2112 test strain shows a higher ($P<0.05$) concentration of IL-10 than cells from strain 4000, 4020 or control mice. Also TGF-beta-2 levels are lower for the SD2112 strain. This strain is selected according to the present invention.

b. Confirmation of Stimulation of IL10 Production and TGF-Beta-2 Reduction in Human Breast Milk by Cells of *Lactobacillus* Strains This example confirms that the selected strain gives the desired effect in vivo. *Lactobacillus reuteri*, ATCC55730 (available from The American Type Culture Collection, Manassas, Va., USA) is tested. The test *Lactobacillus* strain is grown in MRS broth (Difco), and harvested during the exponential growth phase by centrifugation at 1000×g, washed twice with phosphate buffered saline (PBS; pH 6.8) and re-suspended in the same buffer. After this is the culture formulated into an oil-drop product, following the methods in example 3 below.

This study is a double blind, placebo controlled survey confirming the potential of the selected lactic acid bacteria in allergy, conducted at the departments of Paediatrics at the county hospitals of Jönköping, Motala and Norrköping and the University Hospital in Linköping, Sweden.

Pregnant women from families with a history of allergic disease were randomized to orally receive *Lactobacillus reuteri* SD2112, ATCC 55730, daily dose $1 \times 10^8$ CFU or placebo during the four weeks before term. The history of allergic disease was confirmed by a telephone interview by an experienced allergy research nurse. In all, 232 families were included in the trial and equally randomized between the experimental and placebo arm, from January 2001 to April 2003.

Compliance was assessed by collecting all the used bottles of the study product and then estimate what remained in them.

Methods

The present study includes colostrum, obtained within the first 3 days after delivery, and mature milk, obtained at one month after delivery, from 109 of the mothers. The milk samples were collected by using a manual breast pump into sterile plastic tubes and stored at −70° C. until analysis.

After thawing, the milk samples were centrifuged to remove fat and cellular compartments (Böttcher, 2000). The remaining whey was analyzed immediately regarding the content of IL-10 and the rest of the whey was stored in aliquots at −70° C. and later analyzed for TNF-α, IL4, TGF-beta-1, TGF-beta-2, soluble CD14 (sCD14), total IgA, secretory IgA (sIgA) and sodium and potassium.

The levels of TGF-beta-1, TGF-beta-2 and sCD14 (soluble CD14) were analyzed with commercial ELISA kits (R&D Systems, Abingdon, UK) according to the manufacturer's recommendations. The analyses of TGF-beta-1 and TGF-beta-2 were performed after acid treatment to preactivate latent TGF-beta, as described earlier (Böttcher 2000). The levels of IL-10 and TNF-α were determined with commercial ELISA reagent kits (CLB PeliPair reagent set, Amsterdam, the Netherlands) according to the manufacturer's protocol. The lower limit of detection was 62.5 pg/mL for TGF-beta-1 and TGF-beta-2, 250 pg/mL for sCD14, 2.3 pg/mL for IL-10 and 7.8 pg/mL for TNF-α.

Total IgA and sIgA were analyzed with ELISA as described earlier (Böttcher 2002). The lower limit of detection, was 31.2 ng/mL for both assays. Sodium and potassium levels were measured at the Clinical Chemistry Department at Linköping University Hospital according to standard routines (ion selective electrodes). Serum IgE levels to a panel of inhalant allergens were analyzed with UniCap® Pharmacia CAP System™ Phadiatop® (Pharmacia Diagnostics, Uppsala, Sweden).

Statistical Analysis

The size of the study group was calculated assuming 80% power to detect a true difference in clinical manifestations in the *L. reuteri* group compared with the placebo group. The calculation is based on the assumption that clinical manifestations of allergy or eczema occurs in at least 40% of the subjects in the placebo group and can be reduced by half in the experimental group. Subjects needed were 91 subjects that could be evaluated per group and the dropout frequency was assumed to be 25%. A randomization list was performed by an extrinsic company and stratified per centre in block size of four. Total number of subjects needed to enroll based on the calculation above, including the expected dropout frequency and block size, were estimated to be 116 women and their offspring per group.

Ethical Considerations

According to the Helsinki Declaration on medical research with human subjects, the participants received a written information and signed an informed consent. The *L. reuteri* SD2112 test strain in oil was regarded as a well documented and a safe product for both children and adults, and consequently it was not seen as an ethical problem to enroll pregnant women and their offspring.

The study procedures with different tests were also seen as a minor problem regarding the fact that a great proportion of this risk population would develop allergy disease and undergo allergy screening procedures. The protocol was approved by the Ethical Review Board at the University Hospital of Linkoping.

Results

In the study, we examined the effect on breast milk when pregnant women had *Lactobacillus reuteri* strain SD2112 orally 4 weeks prior to delivery.

The maternal profiles comparing the two groups were similar. The numbers of weeks when mothers had daily intake of the study product, did not differ between the two groups, as for exclusive breastfeeding at one month. Discontinuations in the two groups, up to one month of age, were mainly caused by referral to neonatal ward, (one of the exclusion criteria). No differences were seen between the two groups.

In the *L. reuteri* test strain group the cytokine profile in the breast milk was changed by increased level of the anti inflammatory cytokine IL10 in colostrums (median 6.61 pg/mL [range 1.15-150]), than in samples from the mothers in the placebo group (4.78 pg/mL [1.15-150]); p=0.046. Meanwhile a decrease in the level of TGF-beta-2 in the *L. reuteri* SD2112 group was seen. TGF-beta-2 was significantly lower in the *L. reuteri* group (median 674 pg/mL [102.5 -2800] vs. 965 pg/mL [211.7-2800]) than in the placebo group; p=0.020. The levels of the other parameters were similar in the two groups.

Breast milk obtained 4 weeks after delivery and discontinuation of the daily intake of probiotics, showed no difference compare to the placebo group.

EXAMPLE 3

Manufacturing of Products Containing Selected Strain

In this example, a product called "*Reuteri* Drops" is manufactured. The product is an oil-based formulation containing *L. reuteri* SD2112 made for good stability and shelf life. The unique feature of production process is a drying step of the oil to remove most of the water in the oil.

The oil used in the invention herein is a pure edible vegetable oil, preferably sunflower oil. Although an oil such as a pure sunflower oil would not be expected to contain any water, an unexpected effect of the processing step of drying the oil by placing it under vacuum is a significantly increased stability of the lactobacilli in the formulation as shown by increased survival in the formulation of the invention. Therefore, the oil used in the invention should be an oil from which it is possible to remove the water. Although it was previously known that the stability of such cultures is closely correlated with water activity of the formulation, it was not known to dry oil under vacuum for the stabilization of lactobacilli.

Description of the manufacturing process. A flow chart of the preferred manufacturing process is shown in FIG. 1. Details of one such possible process that may be used in the invention herein follow.

Mixing of Ingredients

1 Mix the medium-chain triglyceride (for example, Akomed R, (Karlshamns AB, Karshamn Sweden) and sunflower oil (for example, Akosun, Karlshamns) with silicondioxide, Cab-o-sil M5P, M5P, Cabot) in a Bolz mixing machine/tank (Alfred BOLZ Apparatebau GmbH, Wangen im Allgäu, Germany)

2 Homogenization. A Sine pump and dispax (Sine Pump, Arvada, Colorado) are connected to the Bolz mixer and the mixture is homogenized.

3 Vacuum-drying. The mixture is dried under 10 mBar vacuum in the Bolz tank, for 12 hours.

4 Adding *Lactobacillus reuteri*. About 20 kg of dried oil mixture is moved to a 50 liter stainless steel vessel. *L. reuteri* powder (preferably freeze-dried; the amount of *L. reuteri* used would vary depending on the amount wanted in the oil, but one example would be to add 0.2 kg of culture having $10^{11}$ CFU per g) is added. It is mixed slowly until homogenous.

5 Mixing. The premix with *L. reuteri* is brought back to the Bolz mixer.

6 Discharging. The suspension is discharged to a 200 liter glass vessel, and covered with nitrogen. The suspension is held in the vessel until filling in bottles.

While certain representative embodiments have been set forth herein, those skilled in the art will readily appreciate that modifications can be made without departing from the spirit or scope of the invention.

What is claimed is:

1. A method of producing a stabilized oral oil-containing bacterial formulation, comprising: a) vacuum-drying an edible vegetable oil under conditions suitable to remove the water from said oil, b) providing dried cells of a *Lactobacillus* strain, c) mixing the vacuum-dried oil with the dried cells, and d) producing the stabilized oral formulation, wherein the oil has been vacuum-dried before mixing the dried cells and the oil.

2. A stabilized oral oil-containing bacterial formulation produced according to the method of claim 1, wherein the stabilized *Lactobacillus* cells exhibit increased survival in the vacuum-dried oil.

3. The stabilized oral bacterial formulation of claim 2, wherein the edible vegetable oil is sunflower oil.

4. The stabilized oral bacterial formulation of claim 2, wherein the edible vegetable oil comprises sunflower oil and the formulation further comprises a medium chain triglyceride oil.

5. The stabilized oral bacterial formulation of claim 2, wherein the edible vegetable oil comprises a medium chain triglyceride oil.

6. The stabilized oral bacterial formulation of claim 2, wherein the *Lactobacillus* strain is selected by a method comprising:
   a) administering cells of selected *Lactobacillus* strains to a test mouse; b) isolating and culturing spleen cells from the test mouse; c) quantifying the concentrations of IL-10 and TGF-beta-2 in the spleen cells collected from the test mouse; and d) selecting the *Lactobacillus* strain that increases the concentration of IL-10 and at the same time decreases the concentration of TGF-beta-2 in the spleen cells of said test mouse.

7. The stabilized bacterial formulation of claim 2, wherein the dried cells are freeze-dried.

8. An oral formulation for administration to a woman and improving the woman's breast milk, comprising the stabilized oil-containing bacterial formulation of claim 2.

* * * * *